United States Patent [19]

Ronvig

[11] Patent Number: 5,433,352

[45] Date of Patent: Jul. 18, 1995

[54] LIQUID DISPENSER

[75] Inventor: Jørn Rønvig, Daugaard, Denmark

[73] Assignee: A/S Dumex (Dumex Ltd.), Copenhagen S, Denmark

[21] Appl. No.: 159,468

[22] Filed: Nov. 30, 1993

[30] Foreign Application Priority Data

Dec. 3, 1992 [DK] Denmark ............... 1457/92

[51] Int. Cl.⁶ ............................ B67D 5/42
[52] U.S. Cl. ......................... 222/391; 74/169
[58] Field of Search ............... 222/391, 327; 74/169; 604/209, 224

[56] References Cited

U.S. PATENT DOCUMENTS

| 977,282 | 11/1910 | De Vilbiss . |
| 1,435,908 | 11/1922 | Muehl . |
| 3,517,668 | 6/1970 | Brickson . |
| 4,318,499 | 3/1982 | Hamilton ............... 222/391 X |
| 4,444,560 | 4/1984 | Jacklich . |
| 4,581,022 | 4/1986 | Leonard et al. . |
| 4,744,494 | 5/1988 | Seager et al. ............... 222/391 |
| 4,779,770 | 10/1988 | Herold . |

Primary Examiner—Gregory L. Huson
Attorney, Agent, or Firm—Watov & Kipnes

[57] ABSTRACT

A liquid dispensing device which includes a housing and a spring actuated lever arm hingedly connected to the housing and having a latch operatively connected to a toothed bar wherein upon depression of the lever arm the toothed bar is axially displaced toward the front end of the housing and during return of the lever arm to its original position, the toothed bar is released, wherein the lever arm, the spring and the latch are integral, and the spring and latch are the same element.

7 Claims, 6 Drawing Sheets

LIQUID DISPENSER

FIELD OF THE INVENTION

The present invention relates to a liquid dispenser comprising an elongated housing which at its front end is provided with means for securing a dispensing means thereto, a cavity for holding a liquid and having an axially displaceable piston, a toothed bar which is axially displaceable in said housing and the front end of which is in contact with the piston, a spring-actuated lever arm connected to said housing by means of a hinge device and connected with a latch, the front end of which is in contact with the toothed bar, and upon depression of the lever arm engaging the toothed bar and causing axial displacement thereof towards the front end of the housing and, during the return of the lever arm to its starting position, disengaging from the toothed bar and wherein the lever arm, spring and latch are integral.

BACKGROUND OF THE INVENTION

U.S. Pat. Nos. 4,581,022 and 4,444,560 disclose liquid dispensers comprising a number of separate components. Consequently, the production as well as the assembly costs are so high that there is no economical basis for using them as disposable dispensers.

U.S. Pat. No. 4,779,770 discloses a liquid dispenser of plastics and of the above-mentioned type wherein the rear portion of the housing, the lever arm, the spring and the latch are cast integrally.

In this known liquid dispenser, the hinge connection between the lever arm and the rear portion of the housing is constituted of a wall portion having reduced wall thickness. Consequently, the rotational point of the hinge is not precisely fixed, meaning that the latch extending from the underside of the lever arm does not necessarily engage immediately the toothed bar upon each depression of said lever arm. If the latch slides across one or more tooth (teeth) on the toothed bar the desired dosage is not obtained.

It is the object of the invention to provide a liquid dispenser composed of only a few separate components from which uniform liquid dosages can be obtained.

SUMMARY OF THE INVENTION

This object is obtained according to the invention with a liquid dispenser of the type described above and which is characterized in that the spring and latch are constituted of one and the same element.

By designing the spring and latch as stated above the portion of the latch which causes advancement of the toothed bar upon depression of the lever arm, e.g the latch tip, is maintained in resilient abutment on the toothed bar. It is therefore ensured that the said portion of the latch immediately engages with the toothed bar on depression of the lever arm and that the engagement is maintained during the continued movement of the lever arm.

By suitably shaping the teeth of the toothed bar, which may e.g. have rearwardly oriented tips, the pressure exerted by the latch on the toothed bar does not prevent the latch from sliding across the toothed bar when, following relief of the pressure exerted thereon, the lever arm returns to its starting position. Thus, the return of the lever arm to its starting position does not cause the toothed bar to be withdrawn.

Preferably, the front portion of the elongated housing has a cavity of such form that a liquid-filled ampoule containing an axially displaceable piston may be placed therein.

The housing is preferably cylindrical and conveniently comprises two parts, viz. a front part and a rear part, which are screwed together. Thus, at its rear end the front part may be provided with an internal thread corresponding to an external thread on the front end of the rear part. When using such a housing comprising two parts the lever arm is connected to the rear part by a hinge.

The lever arm preferably has a U-shaped cross section at least at the end where it is connected to the rear part and the hinge connection means is preferably constituted by pins on the insides of the U-shaped portion of the lever arm and corresponding recesses provided on opposite sides of the housing.

Preferably, the portion of the toothed bar which is exposed to the influence of the combined latch and spring has a circular cross section and the portion of the latch which engages with the toothed bar preferably has a correspondingly arched, e.g. semicircular, cross section. In the engagement area the latch is preferably provided with at least two teeth which, during advancement of the toothed bar, engage with two corresponding teeth on the toothed bar. This provides efficient engagement of the latch with the toothed bar and the risk of technical malfunction at this point is almost completely eliminated.

The teeth on the toothed bar may be rearwardly oriented in a known manner so as to allow the latch, during the movement of the lever arm back to its starting postion, to slide across the toothed bar without the latter being withdrawn. For further preventing the toothed bar from withdrawing, the front portion of the rear part is preferably designed with two diametrically opposite resilient jaws which, by engagement with the teeth on the toothed bar, prevent the latter from reverting to its starting position but permit advancement of same.

By also constructing the rear end of the toothed bar with a stopping means, e.g. in the form of a plate element of such dimensions that it cannot pass through the housing, it is ensured that, following advancement to its front position (corresponding to a complete advancement of the piston in the ampoule), the toothed bar is prevented from reverting to its starting position and to be used in connection with a new front part of the housing or a new ampoule. This is of considerable significance when, in order to avoid the transfer of infections, it is desired to prevent reuse of the dispenser.

As mentioned, the front part of the housing has means for securing a dispenser means thereto, e.g. a syringe mounted in a syringe holder. For this use the front end of the housing may comprise a circular flange provided with an internal thread corresponding to the external thread on a syringe holder.

The lever arm and thus the latch integrated therewith may be made of a plastics material, but the housing and the toothed bar are preferably also made of a plastics material. An example of a suitable plastics material is HD polyethylene.

BRIEF DESCRIPTION OF THE DRAWINGS

The invention will now be described in further detail with reference to the drawings, wherein.

DETAILED DESCRIPTION OF THE INVENTION

Figure 1:
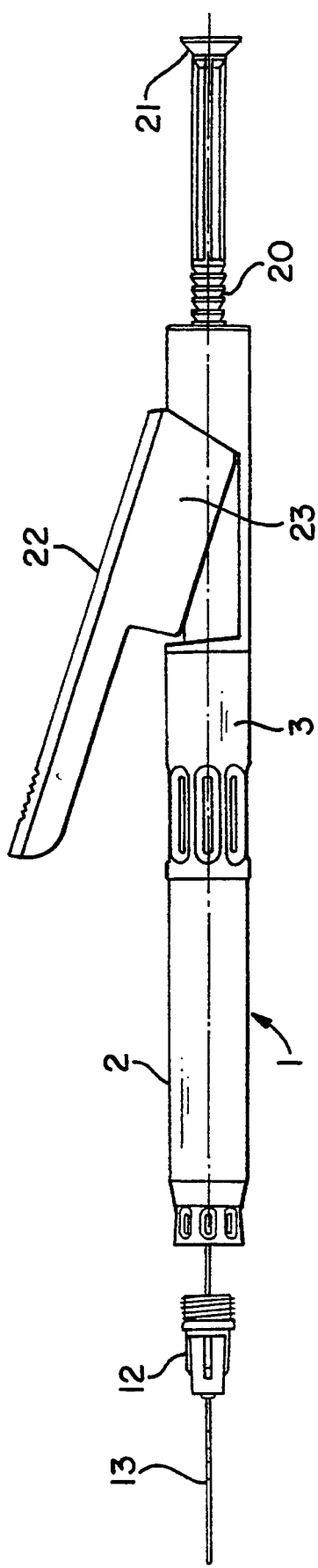
FIG. 1 is a side view of a preferred embodiment of a liquid dispenser according to the invention with a disengaged syringe holder.

The dispenser shown in the drawings comprises a cylindrical housing generally designated 1 and comprising a front part 2 and a rear part 3 which are screwed together. Thus, the front part 2 comprises an internal thread which corresponds to an external thread at the front end of the rear part.

In the front part 2 there is a cavity 4 (See FIG. 2) capable of holding a syringe ampoule 5 containing a liquid 6 maintained between a membrane which is maintained stretched across the neck-shaped ampoule portion by a collar 7 and a piston 8 which is axially displaceable in the ampoule 5.

At the front end of the front part 2 the cavity 4 is delimited by a plate 9 forming the bearing plane of the collar 7 and wherein a central hole is provided. Furthermore, said end of the front part 2 comprises an annular flange 11 having an internal thread corresponding to an external thread on a syringe holder 12 which may be screwed onto the front part, said syringe holder securing a syringe 13 which is pointed at both ends and wherein the rearwardly facing portion of the syringe 13 has sufficient length to extend through the hole 10 in the plate 9, the membrane at the front end of the ampoule 5 and into the interior of the ampoule 5 after the syringe holder 12 has been screwed onto the front part.

As will also appear from the drawings (e.g. FIG. 2) the interior of the housing 1 also comprises a toothed bar 20 which, over some of its length, has a circular cross section and is provided with annular teeth whose tips are rearwardly oriented. At the rear end of said bar a pressure plate 21 is arranged.

The dispenser shown further comprises a U-shaped lever arm 22 wherein the legs of the U are substantially longer at the rear end than at the front end.

Figure 6:
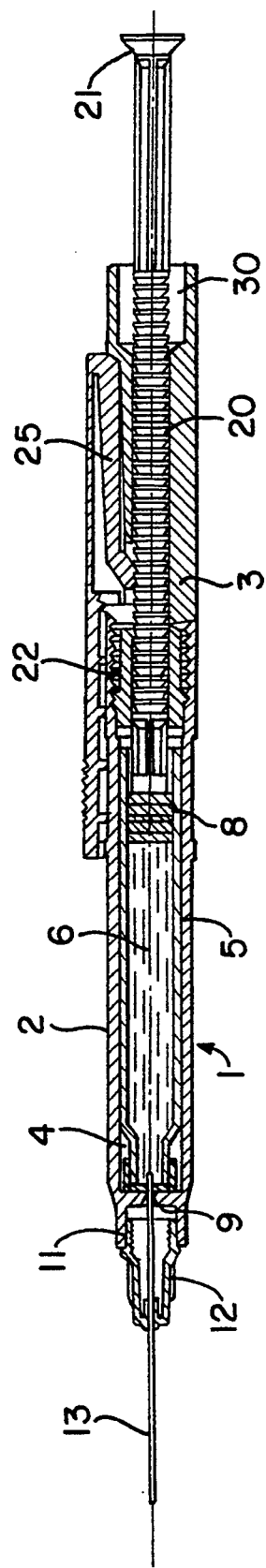
FIG. 6 is a longitudinal sectional view of a dispenser as shown in FIG. 2 following depression of the lever arm.

In the front portion of the lever arm 22 transversally extending support ribs 24 are provided between legs 23 (See FIG. 3), and in the rear end a latch 25 is provided between the legs 23, said latch 25 being moulded integrally with the lever arm 22. In its resting position the latch 25 forms an angle relative to the top surface of the lever arm. The area in which the latch 25 is connected with the lever arm 22, however, has such dimensions that the depression of the lever arm 22 towards the housing 1 causes a reduction of said angle until the top surface of the lever arm 22 reaches a position where the two parts are substantially parallel, as shown best in FIG. 6.

Figure 2:
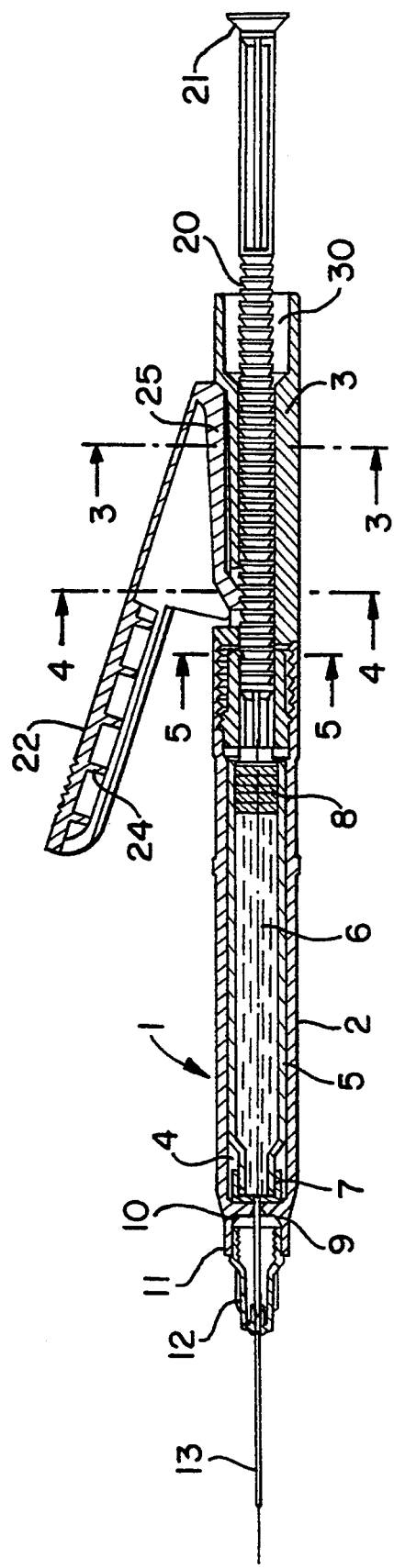
FIG. 2 is a longitudinal sectional view of the dispenser according to FIG. 1 following mounting of a syringe holder.
Figure 3:
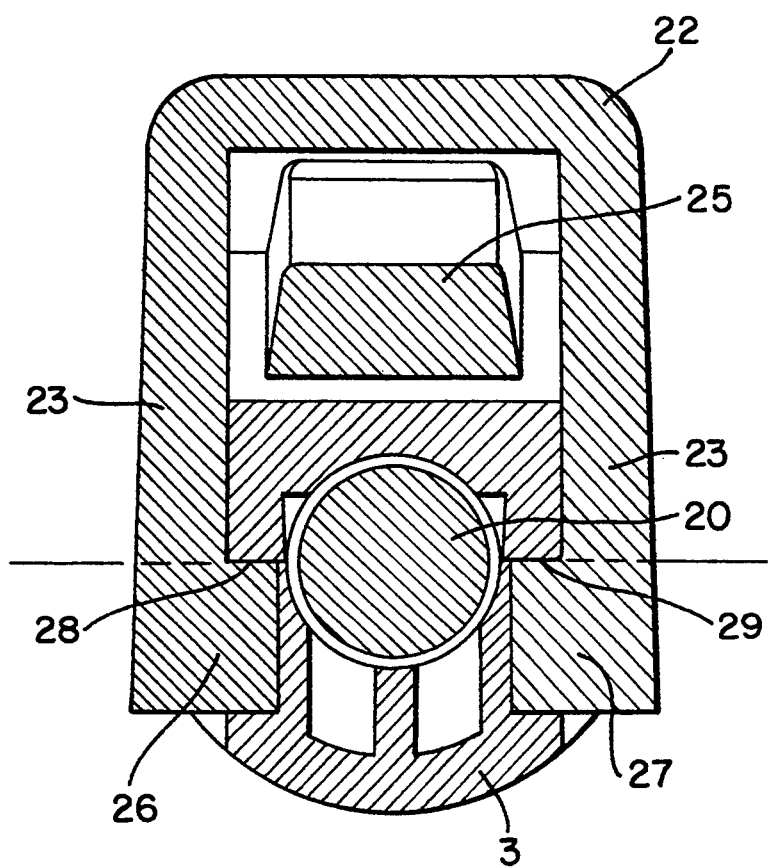
FIG. 3 is a cross sectional view along the line III—III of the dispenser according to FIG. 2.

The lever arm 22 is hinged to the rear portion 3 by means of two pins 26,27 which are inserted in corresponding recesses 28,29 in the sides of the rear part 3, as shown in FIG. 3. A cavity 30 (See FIG. 2) is provided at the rear end of the rear part, said cavity having such dimensions that the pressure plate 21 may be introduced into said cavity.

Figure 4:
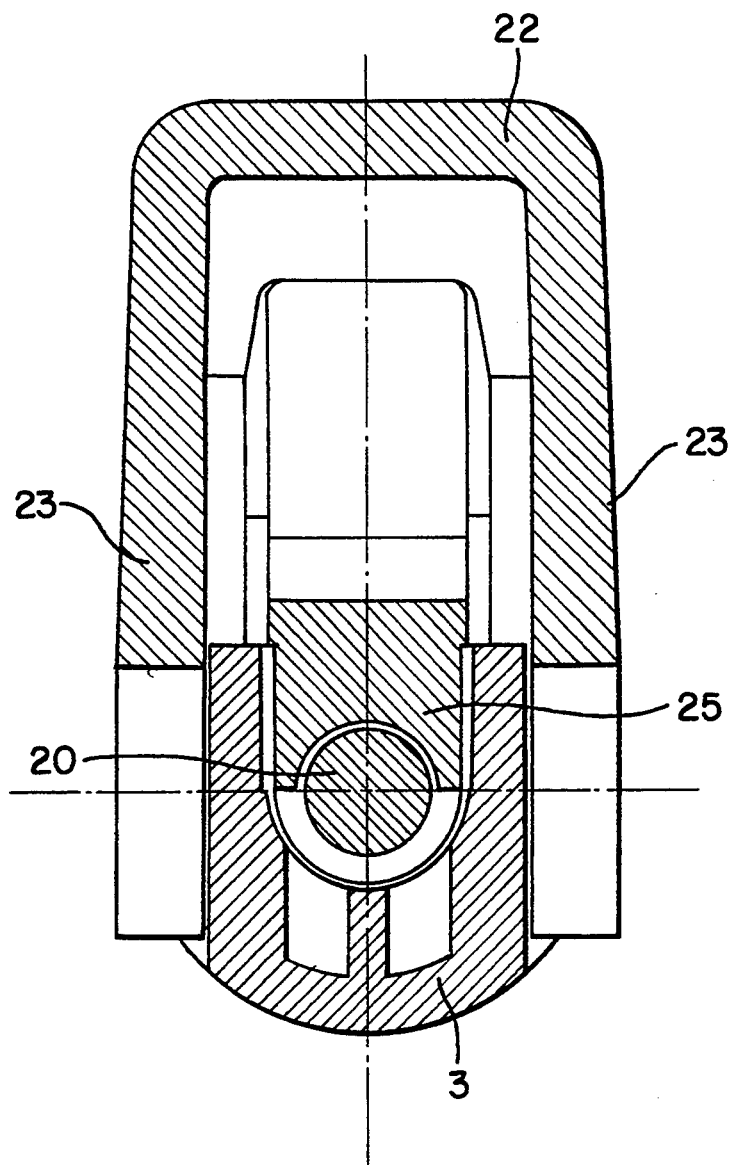
FIG. 4 is a cross sectional view along the line IV—IV of the dispenser according to FIG. 2.

As will appear from FIG. 4 the underside of the front end of the latch 25 has a semicircular shape and is in contact with the toothed bar 20 across half of its periphery.

Figure 5:
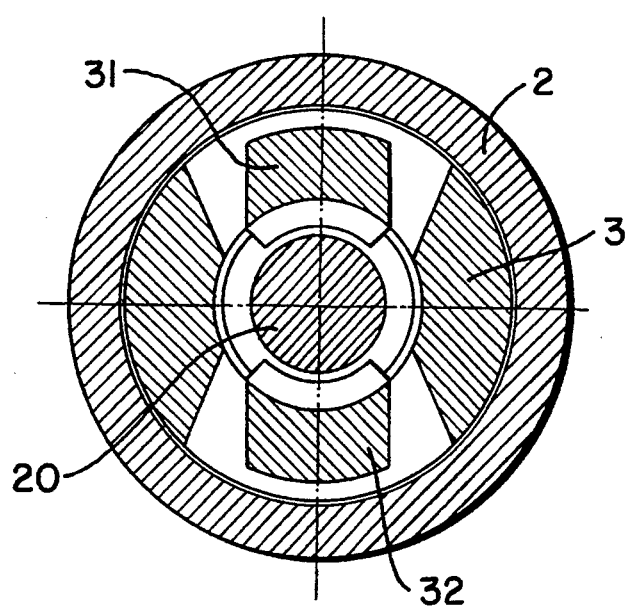
FIG. 5 is a cross sectional view along the line V—V of the dispenser according to FIG. 2.

At the front end of the rear part 3 two diametrically arranged jaws 31 and 32 (See FIG. 5) are provided which at their free ends engage with the toothed bar 20 in a manner corresponding to that of the free end of the latch 25. The jaws 31 and 32, however, extending across a smaller portion of the periphery of the toothed bar 20. The jaws 31 and 32 prevent the toothed bar 20 from moving away from the ampoule 5 but permit movement in the opposite direction.

The dispenser shown operates as follows:

Before being used where the toothed bar 20 occupies a position where the jaws 31 and 32 are engaged with the front teeth of the toothed bar 20, the front part 2 and the rear part 3 are separated and an ampoule 5 is inserted into the cavity 4.

When the front part 2 and the rear part 3 have been screwed together, the toothed bar 20 is advanced to a position in which the front end thereof exerts a pressure on the piston 8 of the ampoule 5 by exerting a pressure on the pressure plate 21. Thereby the ampoule 5 is advanced towards the plate 9 thus causing the rearwardly facing portion of the syringe 13 to pierce the membrane at the front end of the ampoule 5 so as to establish a liquid connection between the interior of the syringe 13 and the liquid 6 in the ampoule 5.

The dispenser is now ready for use and by depressing the lever arm 22 which at its front end engages with the toothed bar 20 the latch 25 pushes the latter a predetermined distance towards the front end of the dispenser. The piston 8 is thereby displaced accordingly and a given amount of liquid is released through the syringe 13.

When the lever arm 22 is disengaged, the spring effect caused by deformation of the area in which the latch 25 is connected with the lever arm 22 will cause it to revert to the starting position shown in FIGS. 1 and 2. During this movement the latch 25 is also withdrawn and the front end thereof slides across the rearwardly oriented teeth on the toothed bar 20 and finally it will occupy such position that a renewed depression of the lever arm 22 causes it to engage with the toothed bar 20. When, following repeated depressions of the lever arm 22, the piston 8 abuts on the neck-shaped portion of the ampoule 5, the pressure plate 21 on the rear end of the toothed bar 20 will be located inside the cavity 30. Thus, it will be impossible to catch the pressure plate 21 and withdraw the toothed bar 20 and, likewise, the toothed bar cannot be withdrawn through the rear part 3 and reintroduced therein.

The jaws 31 and 32 further ensure that the toothed bar 20 is not caused to revert to its starting position since, as mentioned, they prevent the return, but permit the advancement of the toothed bar 20.

I claim:

1. A liquid dispenser comprising an elongated housing having a front end, securing means for securing a liquid dispensing means to the housing, a cavity within the housing for holding a liquid and having an axially displaceable piston, an axially displaceable toothed bar in said housing, a spring actuated depressible lever arm hingedly connected to said housing and capable of performing a latch and spring function, said front end of the housing being in contact with the toothed bar wherein upon depression of the lever arm the toothed bar is axially displaced towards the front end of the housing and, upon release of pressure on the lever arm, the toothed bar is disengaged from the lever arm, said spring and latch being constituted of one and the same element.

2. The liquid dispenser of claim 1 wherein the lever arm has a U-shaped cross section at an end which is connected to the housing and the hinge connection between the lever arm and the housing comprising pins on the inside of the U-shaped portion of the lever arm and corresponding recesses on opposed sides of the housing.

3. The liquid dispenser of claim 1 wherein the toothed bar comprises an active portion, said active portion of the toothed bar having a circular cross section, said combined spring and latch having a front end having a correspondingly arched cross section.

4. The liquid dispenser of claim 1 wherein the housing comprises a front and rear part, the rear part comprising two diametrically opposed resilient jaws located at the front end of the housing, said jaws permitting advancement but preventing the withdrawal of the toothed bar of the housing.

5. The liquid dispenser of claim 1 wherein the toothed bar has a rear end provided with a stopping means which prevents the toothed bar from being passed through the housing towards the front end thereof.

6. The liquid dispenser of claim 1 wherein the securing means at the front end of the housing comprises an annular flange having an internal thread corresponding to an external thread on a syringe holder.

7. The liquid dispenser of claim 1 wherein the lever arm and the latch are made of high density polyethylene.

* * * * *